US010025283B2

United States Patent
Hasegawa et al.

(10) Patent No.: US 10,025,283 B2
(45) Date of Patent: Jul. 17, 2018

(54) CONTROLLER, MANAGER, PLANT CONTROL SYSTEM, AND DATA PROCESSING METHOD

(71) Applicant: Yokogawa Electric Corporation, Musashino-shi, Tokyo (JP)

(72) Inventors: Kenji Hasegawa, Tokyo (JP); Masahiro Sakai, Tokyo (JP)

(73) Assignee: Yokogawa Electric Corporation, Musashino-shi, Tokyo (JP)

( * ) Notice: Subject to any disclaimer, the term of this patent is extended or adjusted under 35 U.S.C. 154(b) by 735 days.

(21) Appl. No.: 14/602,320

(22) Filed: Jan. 22, 2015

(65) Prior Publication Data

US 2015/0212506 A1 Jul. 30, 2015

(30) Foreign Application Priority Data

Jan. 28, 2014 (JP) .................. 2014-013441

(51) Int. Cl.
*G05B 19/042* (2006.01)
*G05B 15/02* (2006.01)
(Continued)

(52) U.S. Cl.
CPC ......... *G05B 19/0426* (2013.01); *G05B 15/02* (2013.01); *G06F 19/3418* (2013.01);
(Continued)

(58) Field of Classification Search
None
See application file for complete search history.

(56) References Cited

U.S. PATENT DOCUMENTS

2004/0222891 A1  11/2004  Ehlers
2005/0251344 A1*  11/2005  Appel ............... G05B 23/0229
                                                       702/19
(Continued)

FOREIGN PATENT DOCUMENTS

JP       61182143 A     8/1986
JP    2006146631 A     6/2006
(Continued)

OTHER PUBLICATIONS

Erik Blasch, "Introduction to Level 5 Fusion: The Role of the User", Handbook of Multisensor Data Fusion: Theory and Practice, Sep. 26, 2008, pp. 503-535.

*Primary Examiner* — Tuan Dao
(74) *Attorney, Agent, or Firm* — Sughrue Mion, PLLC (57) ABSTRACT

A controller includes a calculator configured to receive process data necessary for controlling a plant and vital data indicating a state of a plant worker, the process data being received from a field device, the vital data being received from the plant worker, the calculator calculating first index data and second index data, the first index data indicating a gap between a current one of the process data and a previous one of the process data which is received when the plant is in a normal state, the second index data indicating a gap between a current one of the vital data and a previous one of the vital data which is received when the plant is in the normal state, and a determiner configured to determine health of the plant by using the first index data and the second index data which are calculated by the calculator.

18 Claims, 8 Drawing Sheets

(51) Int. Cl.
  *G06F 19/00*   (2018.01)
  *G16H 50/30*   (2018.01)
(52) U.S. Cl.
  CPC .............. *G05B 2219/42001* (2013.01); *G06F 19/3431* (2013.01); *G16H 50/30* (2018.01)

(56) References Cited

U.S. PATENT DOCUMENTS

| | | |
|---|---|---|
| 2008/0074254 A1 | 3/2008 | Townsend et al. |
| 2009/0322513 A1 | 12/2009 | Hwang et al. |
| 2010/0023359 A1* | 1/2010 | Easo ..................... G06Q 10/06 705/7.37 |
| 2011/0238372 A1* | 9/2011 | Akimoto ............. G05B 23/024 702/182 |
| 2012/0116186 A1* | 5/2012 | Shrivastav ........... A61B 5/0507 600/301 |
| 2012/0290215 A1 | 11/2012 | Adler et al. |
| 2013/0166114 A1* | 6/2013 | Baines .................... B61L 23/06 701/20 |
| 2013/0217350 A1 | 8/2013 | Singh |
| 2014/0207285 A1* | 7/2014 | Sakabe ................. B25J 9/1697 700/259 |
| 2014/0288850 A1* | 9/2014 | Avigdor ................ G05B 11/32 702/19 |

FOREIGN PATENT DOCUMENTS

| | | |
|---|---|---|
| JP | 4258424 B2 | 4/2009 |
| JP | 201258937 A | 3/2012 |
| WO | 0169329 A2 | 9/2001 |
| WO | 2009073852 A1 | 6/2009 |

\* cited by examiner

CONTROLLER, MANAGER, PLANT CONTROL SYSTEM, AND DATA PROCESSING METHOD

BACKGROUND OF THE INVENTION

Field of the Invention

The disclosure relates to a controller, a manager, a plant control system, and a data processing method.

Priority is claimed on Japanese Patent Application No. 2014-013441, filed Jan. 28, 2014, the contents of which are incorporated herein by reference.

Description of Related Art

A DCS (Distributed Control System) is installed in a plant and a factory (hereinafter called simply "plant" as a generic name of them). In the distributed control system, a field device (for example, a measurement device, an operation device, a display device, an alarm device, or other devices) and a controller controlling the field device are connected via a communication unit. By the distributed control system, an advanced automatic operation is implemented. In the distributed control system, process data necessary for a process control is transferred mutually between the controller and the field device.

Recently, a PAM (Plant Asset Management) system is often installed with the distributed control system so as to increase efficiency of the plant to a maximum extent possible. The plant asset management system performed facility maintenance and predictive maintenance of devices and apparatuses installed in the plant, and the plant asset management system maintains and manages the facility in an appropriate state over a long time. In the plant asset management system, a manager which is a core apparatus of the plant asset management system collects data (field data) necessary for the facility management from the field device.

Although the distributed control system and the plant asset management system collect data from the field device basically, in recent years, apparatuses and systems which collect data about operation loads of plant operators and workers (hereinafter called simply "plant worker" as a generic name of them) as well as the data from the field device are developed. For example, Japanese Patent No. 4258424 discloses an apparatus which can obtain the operation load (for example, a number of manipulating) of a plant operator manipulating devices, display a graph of an aging variation (load trend) of the operation load, and analyze by calculating a correlation with the process data and so on.

The recent field devices are digitalized and become intelligent, and most of the recent field devices obtain large amounts of various data. For example, a field device having a self-diagnosis function (function for diagnosing a state of a self-device) obtains data of a current state of the field device. Because the state of the field device can be detected early by obtaining the data, it is preferable for operating the plant safely and effectively.

An accident of the plant can be caused by a human-caused mistake (human error) of the plant worker. For the reason, in recent years, regarding the plant worker as a part of elements of the plant, systems which can collect vital data (biological information) of the plant worker with the various data obtained from the field device and operate the plant with high reliability is developed. The vital data is such as blood pressure, pulse, breathe, and body temperature of the plant worker.

Although the vital data indicating a state of the plant worker is a part of the elements of the plant, the vital data is difficult to use because it is human information. Also, although the vital data affects the operation of the plant greatly, the vital data is rarely used now. Even if a system uses the vital data, the vital data is used solely as data indicating the state of the plant worker. Therefore, the system does not keep a normality of the plant with the vital data and the process data being integrated.

SUMMARY

A controller may include a calculator configured to receive process data necessary for controlling a plant and vital data indicating a state of a plant worker, the process data being received from a field device, the vital data being received from the plant worker, the calculator calculating first index data and second index data, the first index data indicating a gap between a current one of the process data and a previous one of the process data which is received when the plant is in a normal state, the second index data indicating a gap between a current one of the vital data and a previous one of the vital data which is received when the plant is in the normal state, and a determiner configured to determine health of the plant by using the first index data and the second index data which are calculated by the calculator.

DETAILED DESCRIPTION OF THE EMBODIMENTS

The embodiments of the present invention will be now described herein with reference to illustrative preferred embodiments. Those skilled in the art will recognize that many alternative preferred embodiments can be accomplished using the teaching of the present invention and that the present invention is not limited to the preferred embodiments illustrated herein for explanatory purposes.

Object of some embodiments of the present invention is to provide a controller, a manager, a plant control system, and a data processing method, which can utilize the vital data of the plant worker and keep the normality of the plant.

Plant Control System

Figure 1:
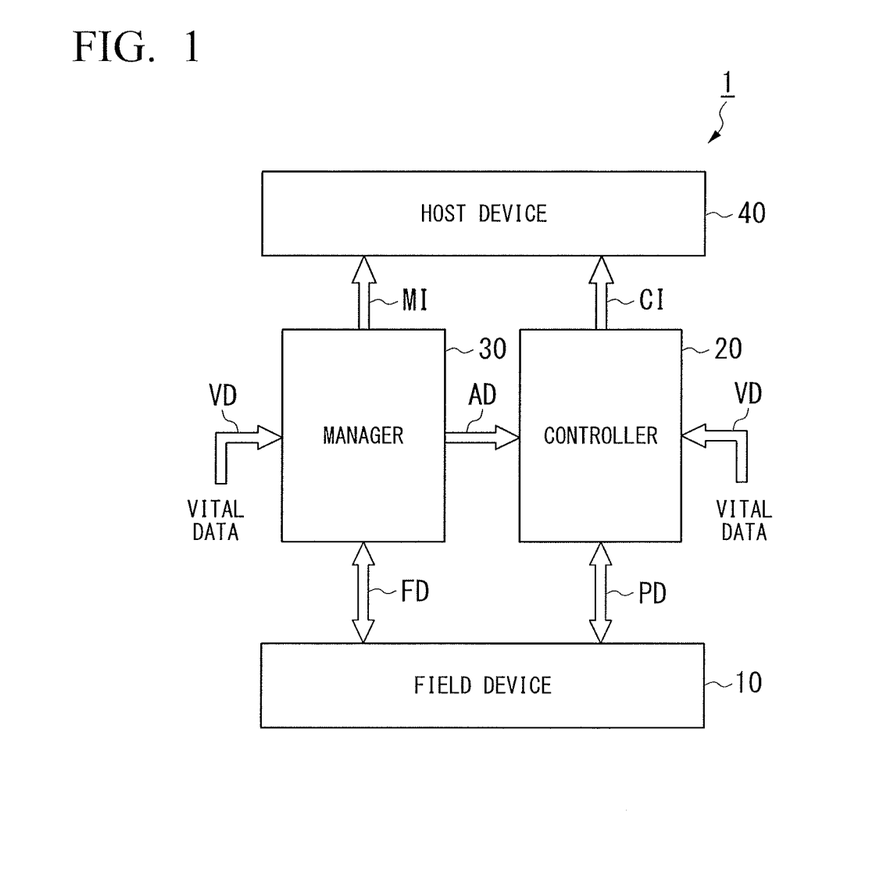
FIG. 1 is a block diagram illustrating a main part of the plant control system in an exemplary embodiment.

FIG. 1 is a block diagram illustrating a main part of the plant control system in an exemplary embodiment. As shown in FIG. 1, the plant control system 1 is equipped with a field device 10, a controller 20, a manager 30, and a host device 40. The plant control system 1 controls an industrial process implemented in the plant (not shown). The plant control system 1 manages facilities such as a device (for example, the field device 10) and apparatus which are installed in the plant. The plant includes an industrial plant such as a chemical industrial plant, a plant managing and controlling a wellhead (for example, a gas field and an oil field), a plant managing and controlling a generation of electric power (for example, water power, fire power, and nuclear power), a plant managing and controlling a power harvesting (for example, solar power and wind power), a plant managing and controlling water supply and sewerage systems, a dam, and so on.

The field device 10 is installed at a field site in the plant, and the field device 10 performs measurements and operations which are necessary for controlling the industrial process under the control of the controller 20. Specifically, the field device 10 is such as a sensor device (for example, a pressure meter, a flowmeter, a temperature sensor, a gas sensor, and a vibration sensor), a valve device (for example, a flow control valve and an on-off valve), an actuator device (for example, a fan and a motor), an imaging device (for example, a camera and a video camera recording circumstances and objects in the plant), a sound device (for example, a microphone collecting abnormal noise in the plant, and a speaker generating alarm sound), a position detection device outputting position information of each device, and other devices. Although a plurality of the field devices are disposed in the plant, to simplify the drawing in FIG. 1, the plurality of the field devices are organized and illustrated as the field device 10.

The field device 10 (each of the field devices installed in the plant) communicates with the controller 20 and the manager 30 which are positioned higher than the field device 10. Also, the field device 10 communicates with the other field devices. For example, the field device 10 communicates with the controller 20, the manager 30, and the other field devices with a wire communication via a network and a communication bus (not shown), or a wireless communication in conformity with an industrial wireless communication standard such as ISA 100.11a, WirelessHART (registered trademark), and so on.

Specifically, as shown in FIG. 1, the field device 10 transmits process data D necessary for a process control to the controller 20 and receives the process data D from the controller 20. For example, the field device 10 transmits measurement data of a state quantity (for example, flow quantity of fluid) in an industrial process to the controller 20, and the field device 10 receives control data (for example, data for controlling the flow quantity of fluid) transmitted from the controller 20.

Also, as shown in FIG. 1, the field device 10 transmits field data FD indicating a state of the field device 10 to the manager 30. The field data FD includes at least one of aged deterioration data indicating an aged deterioration state of the field device 10, stress data indicating a stress of the field device 10, diagnosis data indicating a result of a self-diagnosis performed by the field device 10, and data including alarm data and five senses data. The field data FD can be called big data obtained in the field of the plant.

The controller 20 is a core apparatus of a DCS (Distributed Control System). The controller 20 transmits the process data PD to the field device 10 and receives the process data PD from the field device 10, and the controller 20 controls the industrial process. For example, the controller 20 is operated by a plant operator operating the plant. The controller 20 communicates with the field device 10 and the manager 30. For example, same as the field device 10, the controller 20 communicates with a wire communication via a network and a communication bus (not shown), or a wireless communication in conformity with an industrial wireless communication standard such as ISA 100.11a, WirelessHART (registered trademark), and so on.

Specifically, the controller 20 transmits process data D necessary for the process control to the field device 10 and receives the process data D from the field device 10. For example, the controller 20 receives the measurement data (for example, flow quantity of fluid) transmitted from the field device 10. The controller 20 transmits the control data (for example, data for controlling the flow quantity of fluid) to the field device 10. Also, the controller 20 receives alarm data AD transmitted from the manager 30. The controller 20 transmits control information CI for controlling the plant to the host device 40.

The controller 20 determines health of the plant by using the process data PD obtained from the field device 10 and vital data VD obtained from the plant worker. After that, the controller 20 displays the determination result. For example, the vital data VD is such as blood pressure, pulse, breathe, and body temperature of the plant worker. For example, the vital data VD is obtained by a sensor attached to the plant worker, and the vital data VD is transmitted to the controller 20 and the manager 30. Specific examples of the controller 20 will be described later.

The manager 30 is a core apparatus of the plant asset management (PAM) system. The manager 30 manages the state of the plant by collecting the field data FD from the field device 10. For example, the manager 30 is operated by a worker maintaining the plant. The manager 30 communicates with the field device 10 and the controller 20. Same as the controller 20 of the controller 20, the manager 30 communicates with a wire communication via a network and a communication bus (not shown), or a wireless communication in conformity with an industrial wireless communication standard such as ISA 100.11a, WirelessHART (registered trademark), and so on. Specifically, the manager 30 collects the field data FD transmitted from the field device 10, and the manager 30 transmits the alarm data AD to the controller 20.

The manager 30 calculates the maintenance information MI necessary for managing the state of the plant by using the collected field data FD. Specifically, the manager 30 performs facility maintenance and predictive maintenance of the field device 10 or the like included in the plant, and the manager 30 calculates the maintenance information MI (for example, information indicating an optimum maintenance timing and an optimum exchange timing of the devices) necessary for maintaining and managing the facility in an appropriate state over a long time.

The manager 30 determines health of the plant by using the field data FD obtained from the field device 10 and the vital data VD obtained from the plant worker. After that, the manager 30 displays the determination result. Same as the vital data VD transmitted to the controller 20, the vital data VD is such as blood pressure, pulse, breathe, and body temperature of the plant worker. Also, the vital data VD is obtained by the sensor attached to the plant worker.

The host device 40 is a device for comprehensively monitoring the control state and the management state of the plant. The host device 40 is operated by a manager managing the plant. The host device 40 receives the control information CI transmitted from the controller 20 and the maintenance information MI transmitted from the manager 30. The host device 40 calculates information useful for managing the plant by using the control information CI and the maintenance information MI. The host device 40 displays the calculated information on a display device (not shown).

Controller

Figure 2:
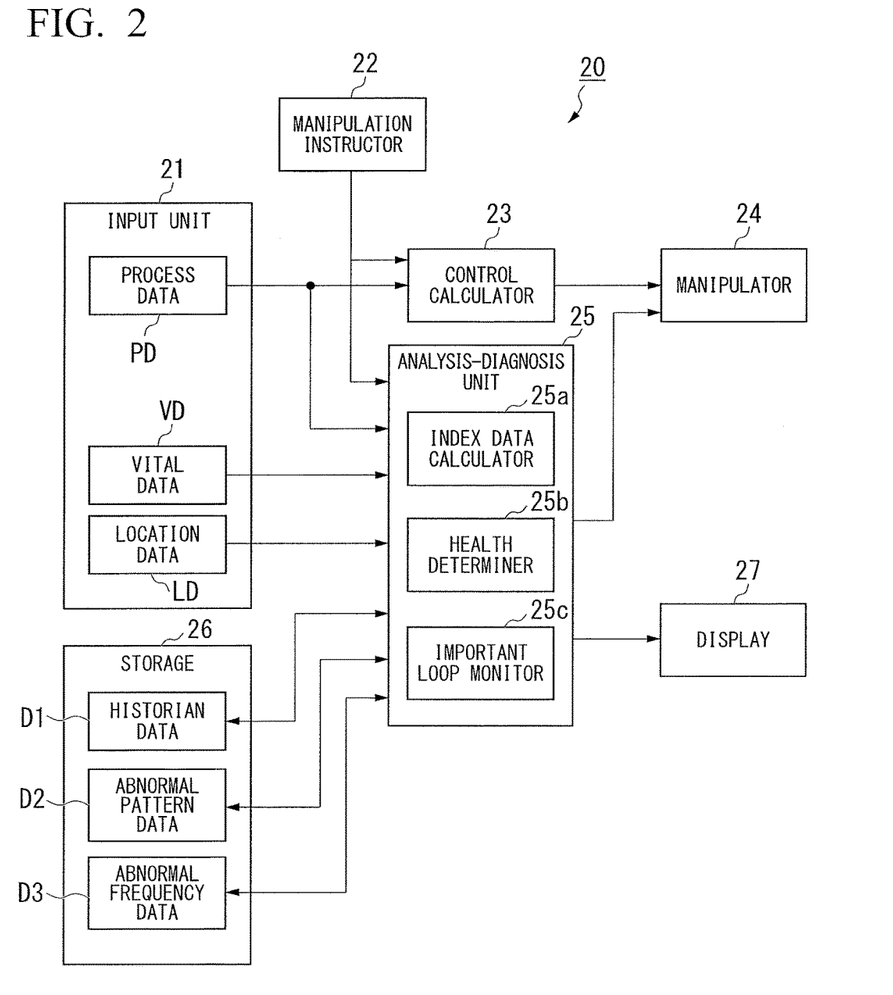
FIG. 2 is a block diagram illustrating a main part of the controller in the exemplary embodiment.

FIG. 2 is a block diagram illustrating a main part of the controller in the exemplary embodiment. As shown in FIG. 2, the controller 20 is equipped with an input unit 21, a manipulation instructor 22, a control calculator 23, a manipulator 24, an analysis-diagnosis unit 25, storage 26, and a display 27. The input unit 21 inputs the process data PD which is transmitted from the field device 10, and the vital data VD and location data LD which are transmitted from the sensor attached to the plant worker. The sensor attached to the plant worker has a positioning function such as GPS (Global Positioning System), and the location data LD indicating the detected position can be transmitted with the vital data VD.

The manipulation instructor 22 is equipped with manipulation devices such as a keyboard and a mouse. For example, the plant operator manipulates the manipulation devices, and the manipulation instructor 22 transmits instructions in accordance with the manipulation by the plant operator. Specifically, the plant operator manipulates the manipulation devices of the manipulation instructor 22. By the manipulation, an instruction for displaying a target value (target temperature, target flow quantity, and so on) of the process control and information to be displayed on the display 27 can be transmitted to the controller 20.

The control calculator 23 calculates a control value for controlling the field device 10 so as to make the process data PD transmitted from the input unit 21 be equal to the target value transmitted from the manipulation instructor 22. For example, the control value is a value for controlling the field device 10 with PID (Proportional-Integral-Derivative) control. The manipulator 24 manipulates in accordance with the control value calculated by the control calculator 23 or a control signal transmitted from the analysis-diagnosis unit 25. Specifically, the manipulator 24 transmits the control signal in accordance with the control value calculated by the control calculator 23 to the field device 10 which is a controlled object. The manipulator 24 performs a manipulation for preventing the field device 10 from malfunctioning and a manipulation for automatically stopping the field device 10.

The analysis-diagnosis unit 25 analyzes and diagnoses the health of the plant by using various types of data input to the input unit 21 and various types of data stored in the storage 26. Specifically, the analysis-diagnosis unit 25 diagnoses the health of the plant by using the process data PD and the vital data VD (additionally, the location data LD) which are input to the input unit 21, and historian data D1 (additionally, abnormal pattern data D2 and abnormality frequency data D3).

The analysis-diagnosis unit 25 has an index data calculator 25*a* (calculator), a health determiner 25*b* (determiner), and an important loop monitor 25*c*. The index data calculator 25*a* calculates index data (first index data) about the process data PD and index data (second index data) about the vital data. The index data indicates a difference (gap) between data obtained when the plant is in a normal state (hereinafter, called "normal state data") and data at present time (hereinafter, called "current data"). "When the plant is in a normal state" means a time when states of processes (states of devices, pipes, and flow quantity, and so on) and a state of the plant worker who is an element of the plant are normal. Specifically, it means a state in which the process data PD obtained from the field device 10 and the vital data VD obtained from the plant worker are within a predetermined normal range.

Specifically, for example, the index data calculator 25*a* calculates the index data about the process data PD by calculating a gap between the process data PD input to the input unit 21 and the process data included in the historian data D1. The process data included in the historian data D1 is the process data input to the input unit 21 when the plant is in a normal state.

In a similar way, for example, the index data calculator 25*a* calculates the index data about the vital data VD by calculating a gap between the vital data VD input to the input unit 21 and the vital data included in the historian data D1. The vital data included in the historian data D1 is the vital data input to the input unit 21 when the plant is in a normal state. Instead of calculating the gap, the index data can be calculated by any one of a method of calculating a change rate, a method of calculating a standard deviation, and other methods. For example, the change rate is a value calculated by dividing current data by the data of the normal state, and the standard deviation is a value representing a deviation of a plurality of the current data with respect to the normal state data.

The health determiner 25*b* determines the health of the plant by using the index data about the process data PD and the index data about the vital data VD which are calculated by the index data calculator 25*a*. Specifically, the health determiner 25*b* determines the health of the plant based on a magnitude relation between the index data about the process data PD and a threshold value (first threshold value) set to the index data about the process data PD and a magnitude relation between the index data about the vital data VD and a threshold value (second threshold value) set to the index data about the vital data VD.

Before determining the health of the plant, the health determiner 25*b* performs a preliminary determination by using the process data PD and the vital data VD which are input to the input unit 21, and the abnormal pattern data D2 and abnormality frequency data D3 which are stored in the storage 26. The health determiner 25*b* performs the preliminary determination so as to improve a determination accuracy of the health of the plant. The important loop monitor 25*c* monitors an important control loop of various types of control loop implemented for the plant control. The important loop monitor 25*c* is provided so as to detect an abnormal of the important control loop quickly and stop automatically and quickly.

The analysis-diagnosis unit 25 sequentially stores the process data PD and the vital data VD in the storage 26 as the historian data D1. The historian data D1 is the process data PD and the vital data VD which are input to the input unit 21 when the plant is normal. In a case where the health determiner 25*b* determines that the health of the plant is abnormal, the analysis-diagnosis unit 25 stores data, in the storage 26, of an abnormal part of the index data about the process data PD and the vital data VD as the abnormal pattern data D2, and the analysis-diagnosis unit 25 stores data, in the storage 26, representing an abnormality frequency of the index data about the process data PD and the vital data VD as the abnormality frequency data D3. A bunch of the data of the abnormal part can be stored as the abnormal pattern data D2 every predetermined period (for example, one day or one week). Also, the abnormality frequency can be stored as the abnormality frequency data D3 every predetermined period.

For example, the storage 26 is equipped with an external storage device such as a hard disc drive. The storage 26 stores the historian data D1, the abnormal pattern data D2 (first backup data), and the abnormality frequency data D3 (second backup data). The display 27 is equipped with a display device such as a liquid crystal display device. The display 27 displays various types of information which is input to the controller 20 or various types of information which is generated by the controller 20. For example, the display 27 displays the process data PD and the vital data VD which are input to the input unit 21, the determination result by the health determiner 25b, and so on. In a case of displaying the determination result by the health determiner 25b, the display 27 displays the determination result of the health of the plant and the determination result of the preliminary determination.

Manager

Figure 3:
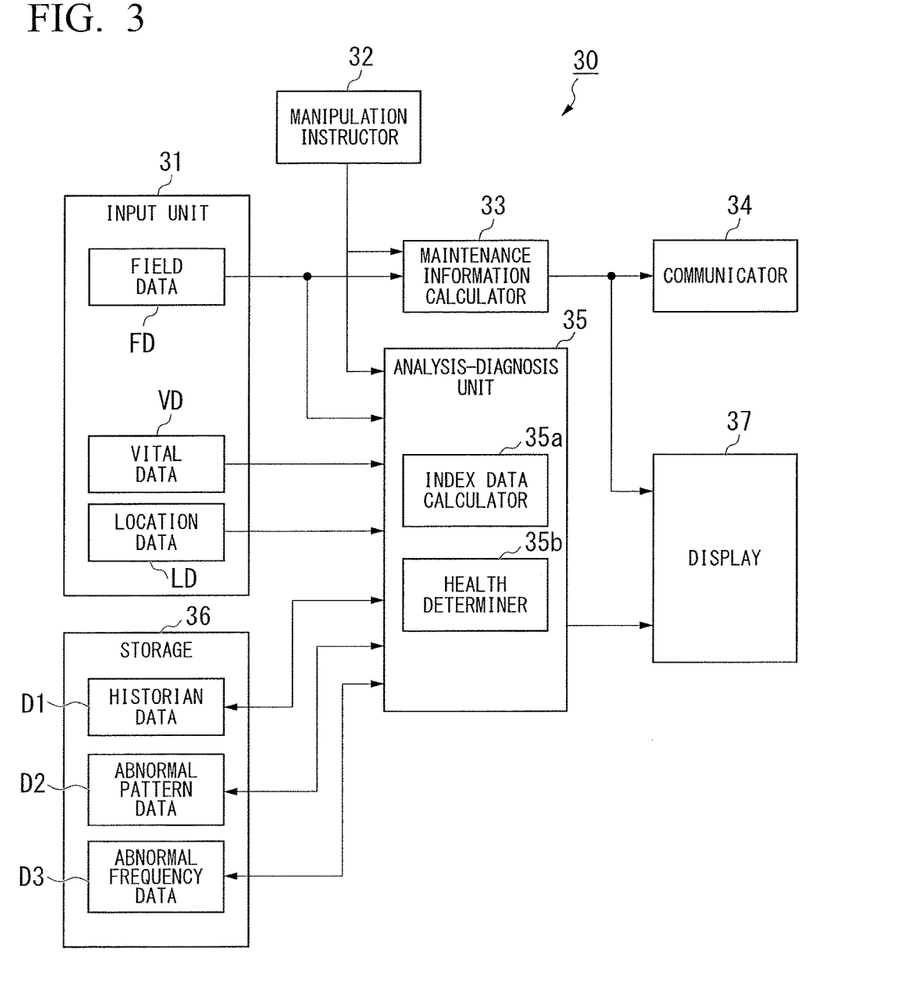
FIG. 3 is a block diagram illustrating a main part of the manager in an exemplary embodiment.

FIG. 3 is a block diagram illustrating a main part of the manager in an exemplary embodiment. As shown in FIG. 3, the manager 30 is equipped with an input unit 31, a manipulation instructor 32, a maintenance information calculator 33, a communicator 34, an analysis-diagnosis unit 35, storage 36, and a display 37. The input unit 31 corresponds to the input unit 21 of the controller 20 shown in FIG. 2. The input unit 31 inputs the field data FD which is transmitted from the field device 10, the vital data VD and the location data LD which are transmitted from the sensor attached to the plant worker.

The manipulation instructor 32 corresponds to the manipulation instructor 22 of the controller 20 shown in FIG. 2. The maintenance information calculator 33 calculates the maintenance information MI necessary for managing the state of the plant by using the field data FD which is input to the input unit 31. Specifically, the maintenance information calculator 33 performs the facility maintenance and the predictive maintenance of the field device 10 or the like included in the plant, and the maintenance information calculator 33 calculates the maintenance information MI (for example, information indicating an optimum maintenance timing and an optimum exchange timing of the devices) necessary for maintaining and managing the facility in an appropriate state over a long time. The communicator 34 communicates with the host device 40. The communicator 34 transmits the maintenance information MI calculated by the maintenance information calculator 33 to the host device 40.

The analysis-diagnosis unit 35 corresponds to the analysis-diagnosis unit 25 of the controller 20 shown in FIG. 2. Although the analysis-diagnosis unit 35 is equipped with an index data calculator 35a and a health determiner 35b corresponds to the index data calculator 25a and the health determiner 25b respectively, a device corresponds to the important loop monitor 25c is omitted. The storage 36 and the display 37 correspond to the storage 26 and the display 27 which are included in the controller 20 respectively.

Operation of Plant Control System

Next, the operation of the plant control system will be described. Hereinafter, the operation of the controller 20 will be described mainly. The controller 20 performs operations for the plant control by transmitting the process data PD to the field device 10 and receiving the process data PD from the field device 10. Specifically, the controller 20 receives the process data PD transmitted from the field device 10 (for example, sensor device) at constant time interval (for example, one second interval). Also, the controller 20 calculates a control value for controlling manipulation amount with respect to the field device 10 (for example, valve device) by using the received process data PD.

The process data PD received by the controller 20 is input to the input unit 21 shown in FIG. 2. The control calculator 23 calculates the control value for controlling the manipulation amount with respect to the field device 10 (for example, valve device). The control value calculated by the control calculator 23 is output to the manipulator 24 and transmitted to the field device 10 (for example, valve device) as a control signal.

When the control signal transmitted from the controller 20 is received by the field device 10, the field device 10 performs a manipulation (for example, controlling an aperture of the valve) in accordance with the control signal. This operation is repeated at constant time interval (for example, one second interval) described above. The control value calculated by the control calculator 23 of the controller 20 is transmitted to the host device 40 as the control information CI.

In parallel with the operations for the plant control, the controller 20 determines the health of the plant. Specifically, the analysis-diagnosis unit 25 determines the health of the plant by using the process data PD and the vital data VD (further, location data LD) which are input to the input unit 21 and the historian data D1 stored in the storage 26.

Figure 4:
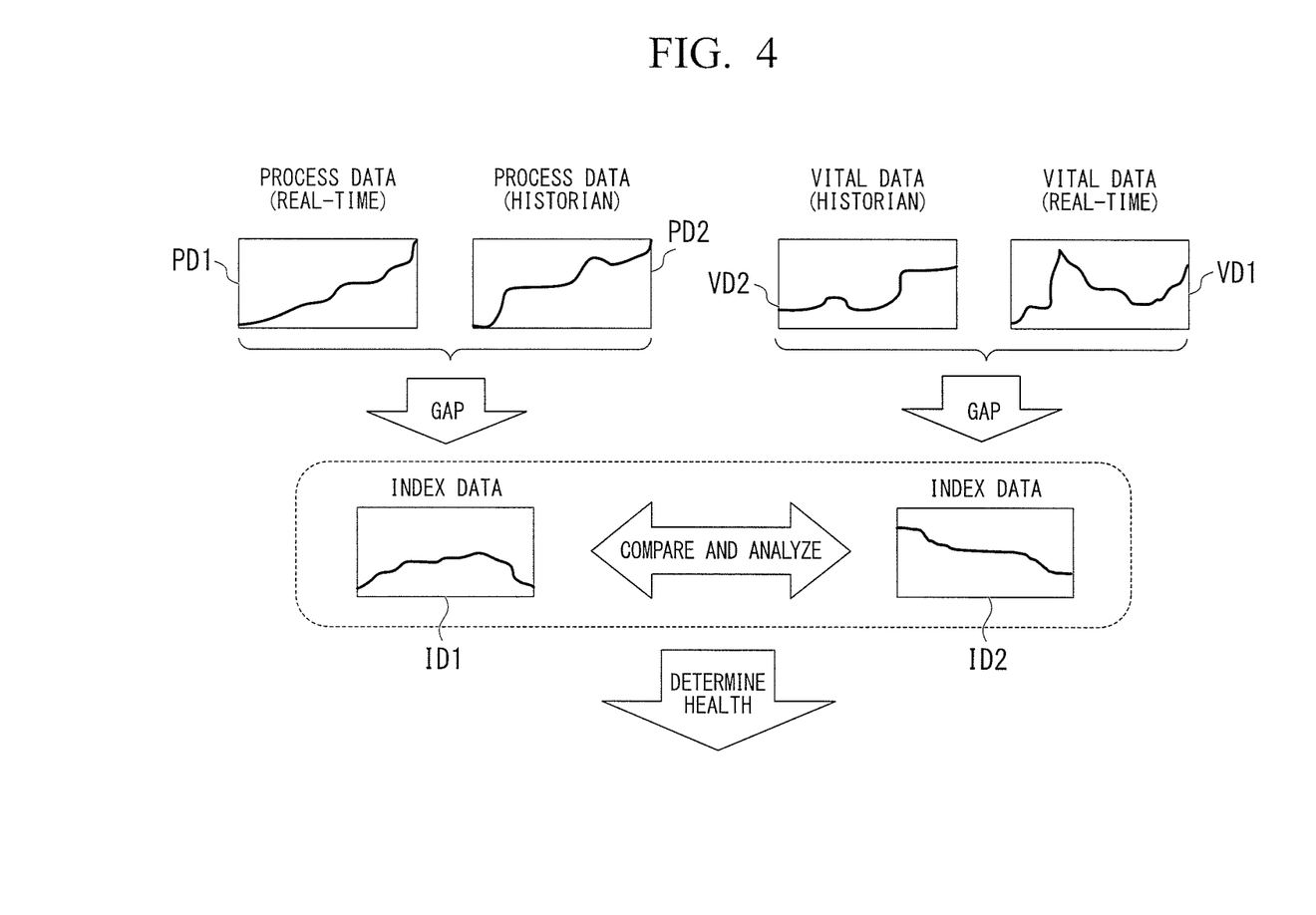
FIG. 4 is a drawing for describing a health determination process performed by the controller in an exemplary embodiment.

FIG. 4 is a drawing for describing a health determination process performed by the controller in an exemplary embodiment. First, as shown in FIG. 4, the index data calculator 25a of the analysis-diagnosis unit 25 calculates a gap between a current one of the process data PD (process data PD1 shown in FIG. 4) which is received at a present time and a previous one of the process data PD (process data PD2 shown in FIG. 4) which is received when the plant is in a normal state. The previous one of the process data PD is included in the historian data D1 which is stored in the storage 26. By this calculation, the index data (index data ID1 shown in FIG. 4) about the process data PD is calculated.

In parallel with the process described above, the index data calculator 25a of the analysis-diagnosis unit 25 calculates a gap between a current one of the vital data VD (vital data VD1 shown in FIG. 4) which is received at a present time and a previous one of the vital data VD (vital data VD2 shown in FIG. 4) which is received when the plant is in a normal state. The previous one of the vital data VD is included in the historian data D1 which is stored in the storage 26. By this calculation, the index data (index data ID2 shown in FIG. 4) about the vital data VD is calculated.

The index data ID1 about the process data PD and the index data ID2 about the vital data VD which are calculated by the index data calculator 25a are input to the health determiner 25b. As shown in FIG. 4, the health determiner 25b determines the health of the plant. Specifically, the health determiner 25b determines the magnitude relation between the index data ID1 about the process data PD and the predetermined threshold value (first threshold value), and the health determiner 25b determines the magnitude relation between the index data ID2 about the vital data VD and the predetermined threshold value (second threshold value). The health determiner 25b determines the health of the plant based on these magnitude relations.

Figure 5:
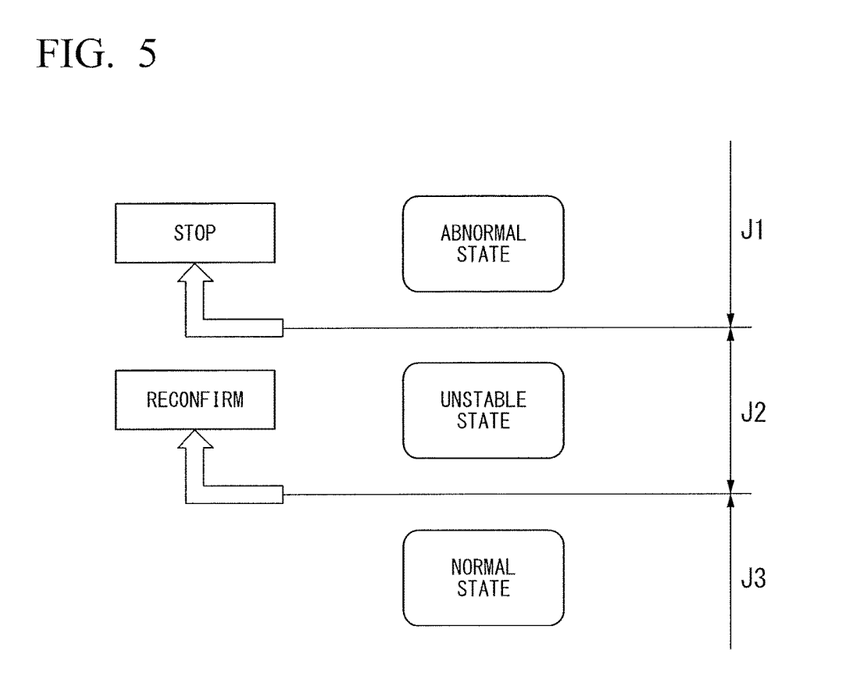
FIG. 5 is a drawing illustrating a determination result of the health in an exemplary embodiment.

FIG. 5 is a drawing illustrating a determination result of the health in an exemplary embodiment. As shown in FIG. 5, the determination results of the health determiner 25b are categorized into three determination results J1 through J3 described below.

(a) Determination Result J1: "Abnormal State"

For example, the "abnormal state" means a state in which an abnormality with which the plant operator cannot deal is generated, and the process should be stopped.

(b) Determination Result J2: "Unstable State"

For example, the "unstable state" means a state in which the plant operator is likely to make an operation mistake, and there is a need to reconfirm the operation performed by the plant operator.

(c) Determination Result J3: "Normal State"

For example, the "normal state" means a state in which the plant operator is normal, and there is no abnormality of the plant and the plant operator.

For example, in a case where the index data ID1 exceeds the threshold, the determination result of the health determiner 25b is the "abnormal state" (determination result J1) regardless of whether the index data ID2 exceeds the threshold. In a case where the index data ID1 does not exceed the threshold and the index data ID2 exceeds the threshold, the determination result of the health determiner 25b is the "unstable state" (determination result J2). In a case where both of the index data ID1 and the index data ID2 do not exceed the threshold, the determination result of the health determiner 25b is the "normal state" (determination result J3). Especially, in a case of the determination result J2, the plant operator can deal with the possibility of making an operation mistake which occurs when the process data is normal and the vital data of the plant worker is abnormal.

For example, in a case where the determination result of the health determiner 25b is the "abnormal state" (determination result J1), the manipulator 24 stops the plant by making the field device 10 stop automatically, and the manipulator 24 informs the host device 40 of the occurrence of the abnormality. Especially, it is effective for an abnormal state of the important loop monitored by the important loop monitor 25c. For example, in a case where the determination result of the health determiner 25b is the "unstable state" (determination result J2), the manipulator 24 informs the plant operator of reconfirming the operation performed by the plant worker. In a case where the determination result of the health determiner 25b is the "normal state" (determination result J3), a special operation and a special process are not performed and the current operation is continued.

Figure 6:
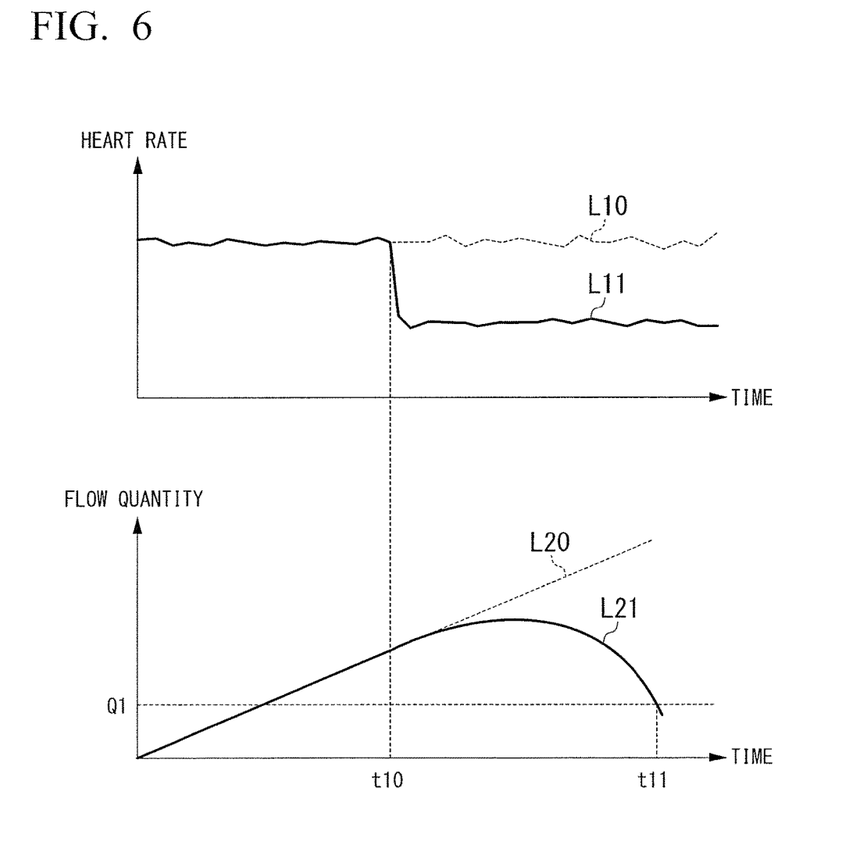
FIG. 6 is a drawing illustrating the process data and the vital data in an exemplary embodiment.

FIG. 6 is a drawing illustrating the process data and the vital data in an exemplary embodiment. As shown in FIG. 6, the flow quantity is an example of the process data PD, and the heart rate of the plant worker is an example of the vital data VD. In a case where the abnormality of the plant and the abnormality of the plant worker do not occur, the heart rate of the plant worker is approximately constant (refer to the curved line L10), and the flow quantity is increased gradually at a constant rate (refer to the curved line L20).

As shown in FIG. 6, at the time t10, an abnormality of the plant worker occurs and the heart rate of the plant worker is decreased drastically (refer to the curved line L11). At this time, in a case where an operation which the plant worker should perform is not performed, for example, the flow quantity is decreased gradually, and thereafter the flow quantity is decreased drastically (refer to the curved line L21). For example, although the plant worker must increase the flow quantity (refer to the curved line L20), the plant worker might decrease the flow quantity by a determination mistake and an operation mistake caused by an abnormality of the heart rate (refer to the curved line L21).

Conventionally, because of referring to only the process data PD, the occurrence of the plant accident can be detected at the time t11 when the flow quantity falls below a lower limit Q1. On the other hand, in the present embodiment, the index data calculator 25a calculates the index data (a gap between the curved line L20 and L21) about the process data PD (flow quantity) and the index data (a gap between the curved line L10 and L11) about the vital data VD (heart rate), and the health determiner 25b determines the health of the plant based on these index data. For the reason, within short time lapsed from the time t11 when the abnormality of the operator occurred, an abnormality of the plant can be determined at an early point.

Figure 7:
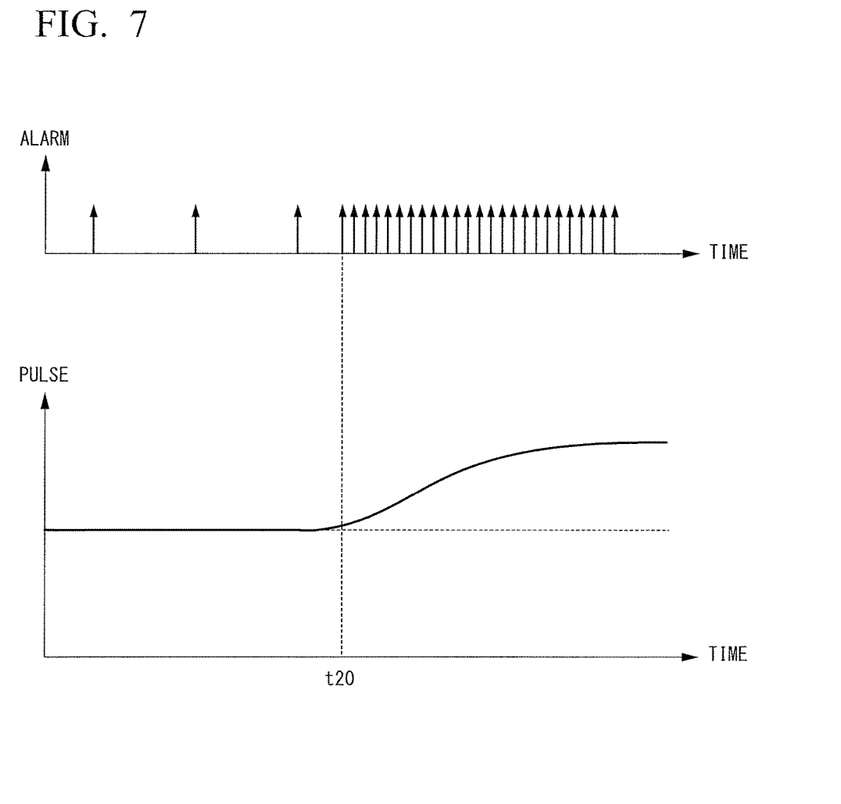
FIG. 7 is a drawing illustrating another example of the process data and the vital data in an exemplary embodiment.

FIG. 7 is a drawing illustrating another example of the process data and the vital data in an exemplary embodiment. As shown in FIG. 7, the alarm is an example of the process data PD, and the pulse of the plant operator is an example of the vital data VD. In a case where the abnormality of the plant and the abnormality of the plant worker do not occur (until the time t20), the alarm is generated at approximately constant time interval (the alarm frequency is approximately constant), and the pulse is approximately constant.

As shown in FIG. 7, at the time t20, an abnormality of the plant occurs and the alarm is increased drastically (the alarm frequency is increased drastically). At this time, for example, it is necessary that the plant operator should determine a type of the alarm and a reason for generating the alarm, and the plant operator should deal with the alarm. For this reason, as shown in FIG. 7, the pulse of the plant operator is increased. At this time, in a case where the generated alarm is important, the pulse of the plant operator might be increased drastically in a high stress situation.

Conventionally, the generated alarm is merely informed to the plant operator basically. On the other hand, in the present embodiment, the index data calculator 25a calculates the index data (a gap between an alarm frequency at the normal state and an alarm frequency at the abnormal state) about the process data PD (alarm) and the index data (a gap between a pulse at the normal state and a pulse at the abnormal state) about the vital data VD, and the health determiner 25b determines the health of the plant based on these index data. Conventionally, with reference to only the process data (alarm), in a case where the number of the alarm is increased within a constant time interval, the abnormality of the plant is determined. On the other hand, by using both of the index data about the process data PD and the index data about the vital data VD, within short time lapsed from the time t20 when the abnormality of the plant occurred, an abnormality of the plant can be determined at an early point.

As shown in FIG. 2, in a case where the abnormal pattern data D2 and the abnormality frequency data D3 is stored in the storage 26, the health determiner 25b performs the preliminary determination by using the abnormal pattern data D2 and the abnormality frequency data D3 before the health determiner 25b determines the health of the plant by using the index data ID1 and the index data ID2 described in FIG. 4. For example, the plant worker can indicate whether the preliminary determination is performed or not by manipulating the manipulation instructor 22.

Specifically, for example, the health determiner 25b performs a pattern matching process with respect to the index data about the process data PD and the vital data VD, which are input to the input unit 21, and the abnormal pattern data D2 stored in the storage 26. Also, the health determiner 25b determines whether the index data about the process data PD and the vital data VD which are input to the input unit 21 is similar to the abnormal pattern data D2 stored in the storage 26 or not. In a case where a degree of the similarity is high, the process data PD and the vital data VD, which are input to the input unit 21, are similar to the process data PD and the vital data VD which are obtained when an abnormality occurred in the past. For the reason, the health determiner 25*b* can determine that, at the preliminary determination, an abnormality occurred in the plant. Same as this, a degree of the similarity between the abnormality frequency of the index data about the process data PD and the vital data VD, which are input to the input unit 21, and the abnormality frequency data D3 is high, the health determiner 25*b* can determine that, at the preliminary determination, an abnormality occurred in the plant.

Figure 8A:
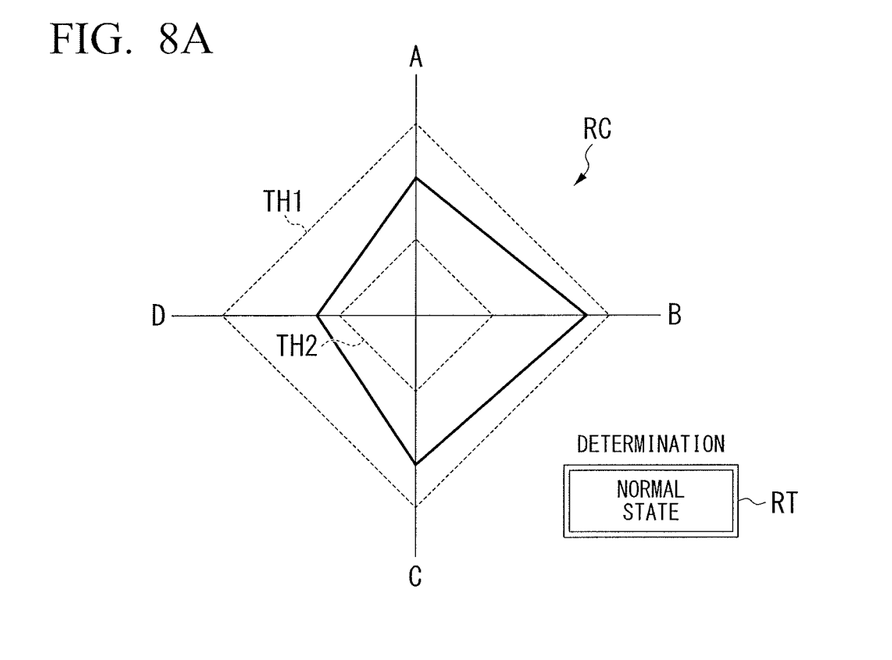
FIG. 8A is a drawing illustrating an example of a display in a case where the determination result is the normal state.
Figure 8B:
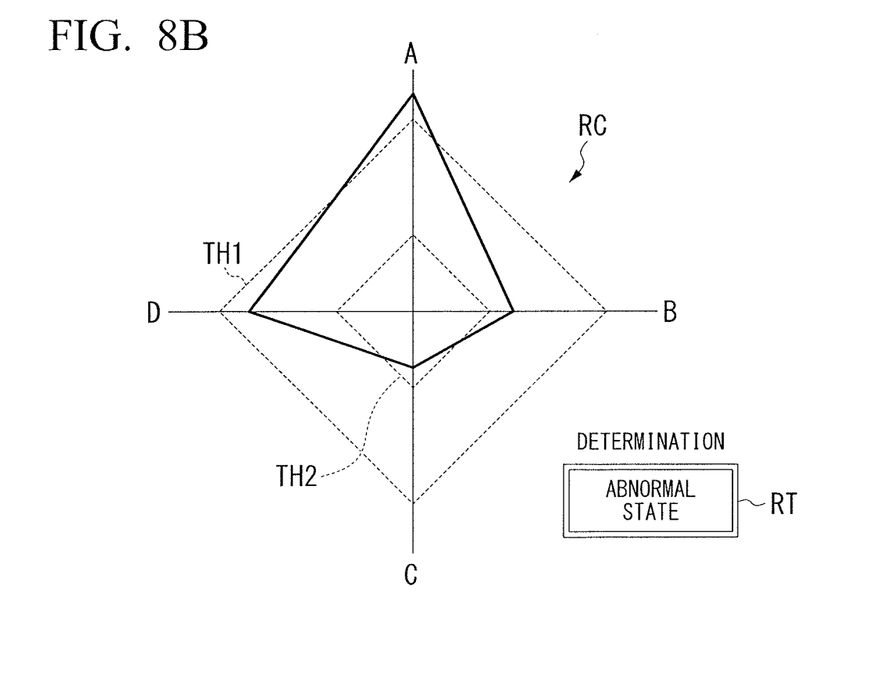
FIG. 8B is a drawing illustrating an example of a display in a case where the determination result is the abnormal state.

FIG. 8A is a drawing illustrating an example of a display in a case where the determination result is the normal state. FIG. 8B is a drawing illustrating an example of a display in a case where the determination result is the abnormal state. As shown in FIG. 8A and FIG. 8B, a radar chart RC including four axes (axes A through D) and a determination result display area RT indicating a final determination result are displayed on the display 27 of the controller 20.

The axis A of the radar chart RC indicates the index data ID1 about the process data PD. The axis B of the radar chart RC indicates the index data ID2 about the vital data VD. On the axis A of the radar chart RC, a current value (most recent value) of the index data ID1 or a value obtained by performing a predetermined calculation (for example, a moving average calculation) with respect to the index data ID1 is plotted. Also, on the axis B of the radar chart RC, a current value (most recent value) of the index data ID2 or a value obtained by performing a predetermined calculation (for example, a moving average calculation) with respect to the index data ID2 is plotted.

The axes C and D indicate the preliminary determination result. Specifically, the axis C indicates the preliminary determination result performed by using the process data PD and the vital data VD, which are input to the input unit 21, and the abnormal pattern data D2 stored in the storage 26. Also, the axis D indicates the preliminary determination result performed by using the process data PD and the vital data VD, which are input to the input unit 21, and the abnormality frequency data D3 stored in the storage 26.

The broken line TH1 (first line) shown in FIGS. 8A and 8B is a line connecting upper allowable limits on the axes A through D. The broken line TH2 (second line) shown in FIGS. 8A and 8B is a line connecting lower allowable limits on the axes A through D. The broken-solid line shown in FIGS. 8A and 8B is a line connecting values on the axes A through D.

As shown in FIG. 8A, in the radar chart RC, all of the index data ID1, the index data ID2, and the preliminary determination results are between the upper allowable limits and the lower allowable limits. With reference to the determination result display area RT, it can be recognized at a glance that the final determination result is "normal state".

As shown in FIG. 8B, in the radar chart RC, the index data ID1 exceeds the upper allowable limit and the preliminary determination result plotted on the axis C falls below the lower allowable limit. With reference to the determination result display area RT, it can be recognized at a glance that the final determination result is "abnormal state".

As described above, in the present embodiment, the controller 20 calculates the index data ID1 indicating the gap between the process data PD obtained from the field device 10 and the process data PD obtained from the field device 10 when the plant is normal. The controller 20 calculates the index data ID2 indicating the gap between the vital data VD obtained from the field device 10 and the vital data VD obtained from the field device 10 when the plant is normal.

The controller 20 determines the health of the plant based on the index data ID1 and the index data ID2. Also, the manager 30 determines the health of the plant by performing the same process. In the present embodiment, the health of the plant is determined by using the process data PD (or the field data FD) and the vital data VD, and the plant worker can take measures appropriately before the plant becomes abnormal. Therefore, the normality of the plant can be maintained.

Although a controller, a manager, a plant control system, and a data processing method according to embodiments of the present invention have been described above, the present invention is not restricted to the above-described embodiments, and can be freely modified within the scope thereof. For example, the foregoing descriptions of the embodiments have been examples in which the health of the plant is determined by using the process data PD and the vital data VD which are obtained in real-time. However, the process data PD and the vital data VD may be stored in a storage device such as a hard disc drive, and the health of the plant may be determined by reading the process data PD and the vital data VD from the storage device when the need to determine the health of the plant comes.

Although the foregoing descriptions of the embodiments have been examples in which the health of the plant is determined by using the process data PD and the vital data VD, the health of the plant may be determined by using the location data LD along with the process data PD and the vital data VD. For example, in a case where a worker has worked on a top of a tank for a long time, considering a working environment of the worker based on the location data LD, the health state (for example, a state of dehydration under the blazing sun) of the worker may be predicted.

Although the foregoing descriptions of the embodiments have been examples in which the health of the plant is determined by using the field data FD and the vital data VD, the health of the plant may be determined by using the location data LD along with the field data FD and the vital data VD. For example, in a case where a worker has worked on a top of a tank for a long time, considering a working environment of the worker based on the location data LD, the health state (for example, a state of dehydration under the blazing sun) of the worker may be predicted.

Although the foregoing descriptions of the embodiments have been examples in which the controller 20 and the manager 30 are separate devices, the controller 20 and the manager 30 may be integral with each other. At least one of the controller 20 and the manager 30 may be a cloud computer.

As used herein, the following directional terms "forward, rearward, above, downward, right, left, vertical, horizontal, below, transverse, row and column" as well as any other similar directional terms refer to those directions of an apparatus equipped with the present invention. Accordingly, these terms, as utilized to describe the present invention should be interpreted relative to an apparatus equipped with the present invention.

The terms of degree such as "substantially," "about," and "approximately" as used herein mean a reasonable amount of deviation of the modified term such that the end result is not significantly changed. For example, these terms can be construed as including a deviation of at least ±5 percents of the modified term if this deviation would not negate the meaning of the word it modifies.

The term "configured" is used to describe a component, unit or part of a device includes hardware and/or software that is constructed and/or programmed to carry out the desired function.

Moreover, terms that are expressed as "means-plus function" in the claims should include any structure that can be utilized to carry out the function of that part of the present invention.

The term "unit" is used to describe a component, unit or part of a hardware and/or software that is constructed and/or programmed to carry out the desired function. Typical examples of the hardware may include, but are not limited to, a device and a circuit.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A controller comprising:
    a hardware calculator or calculator stored in a memory configured to receive process data necessary for controlling a plant and vital data indicating biological information of a plant worker, the process data being received from a field device, the vital data being received from the plant worker, the calculator calculating first index data and second index data, the first index data indicating a gap between a current one of the process data and a previous one of the process data which is received when the plant is in a normal state, the second index data indicating a gap between a current one of the vital data and a previous one of the vital data which is received when the plant is in the normal state;
    a determiner configured to determine health of the plant by using the first index data and the second index data which are calculated by the calculator, the health of the plant including an abnormal state, an unstable state, and a normal state,
    wherein the determiner is configured to determine the health of the plant based on a magnitude relation between the first index data and a first threshold value set to the first index data and a magnitude relation between the second index data and a second threshold value set to the second index data,
    wherein the determiner determines that the plant is in the abnormal state in a case where the first index data exceeds a first threshold value,
    wherein the determiner determines that the plant is in the unstable state in a case where the first index data does not exceed the first threshold value and the second index data exceeds a second threshold value, and
    wherein the determiner determines that the plant is in the normal state in a case where the first index data does not exceed the first threshold value and the second index data does not exceed the second threshold value.

2. The controller according to claim 1, further comprising storage configured to store first backup data and second backup data, the first backup data being data of an abnormal part of the first index data and the second index data, the second backup data being data indicating an abnormality frequency of the first index data and the second index data,
    wherein the determiner is configured to perform a preliminary determination by using at least one of the first backup data and the second backup data before the determiner determines the health of the plant by using the first index data and the second index data.

3. The controller according to claim 2, further comprising a display configured to display a determination result of the health of the plant, which is determined by using the first index data and the second index data, and a determination result of the preliminary determination, which is determined by using the first backup data and the second backup data.

4. The controller according to claim 3, wherein the display is configured to display a radar chart of which axes indicate the first index data, the second index data, and the preliminary determination result.

5. The controller according to claim 4, wherein the display is configured to display the radar chart with a first line connecting upper allowable limits on the axes and a second line connecting lower allowable limits on the axes.

6. The controller according to claim 1, further comprising a display configured to display a determination result of the determiner.

7. The controller according to claim 1, wherein the calculator is configured to receive location data from the plant worker, the location data indicating a location of the plant worker.

8. The controller according to claim 7, wherein the determiner is configured to determine the health of the plant by using the process data, the vital data, and the location data.

9. A manager comprising:
    a hardware calculator or calculator stored in memory configured to receive field data indicating a state of a field device installed in a plant and vital data indicating biological information of a plant worker, the field data being received from the field device, the vital data being received from the plant worker, the calculator calculating first index data and second index data, the first index data indicating a gap between a current one of the field data and a previous one of the field data which is received when the plant is in a normal state, the second index data indicating a gap between a current one of the vital data and a previous one of the vital data which is received when the plant is in the normal state;
    a determiner configured to determine health of the plant by using the first index data and the second index data which are calculated by the calculator, the health of the plant including an abnormal state, an unstable state, and a normal state,
    wherein the determiner is configured to determine the health of the plant based on a magnitude relation between the first index data and a first threshold value set to the first index data and a magnitude relation between the second index data and a second threshold value set to the second index data,
    wherein the determiner determines that the plant is in the abnormal state in a case where the first index data exceeds a first threshold value,
    wherein the determiner determines that the plant is in the unstable state in a case where the first index data does not exceed the first threshold value and the second index data exceeds a second threshold value, and
    wherein the determiner determines that the plant is in the normal state in a case where the first index data does not exceed the first threshold value and the second index data does not exceed the second threshold value.

10. The manager according to claim 9, further comprising storage configured to store first backup data and second backup data, the first backup data being data of an abnormal part of the first index data and the second index data, the second backup data being data indicating an abnormality frequency of the first index data and the second index data,
wherein the determiner is configured to perform a preliminary determination by using at least one of the first backup data and the second backup data before the determiner determines the health of the plant by using the first index data and the second index data.

11. The manager according to claim 10, further comprising a display configured to display a determination result of the health of the plant, which is determined by using the first index data and the second index data, and a determination result of the preliminary determination, which is determined by using the first backup data and the second backup data.

12. The manager according to claim 11, wherein the display is configured to display a radar chart of which axes indicate the first index data, the second index data, and the preliminary determination result.

13. The manager according to claim 12, wherein the display is configured to display the radar chart with a first line connecting upper allowable limits on the axes and a second line connecting lower allowable limits on the axes.

14. The manager according to claim 9, further comprising a display configured to display a determination result of the determiner.

15. The manager according to claim 9, wherein the calculator is configured to receive location data from the plant worker, the location data indicating a location of the plant worker.

16. The manager according to claim 15, wherein the determiner is configured to determine the health of the plant by using the field data, the vital data, and the location data.

17. A plant control system comprising:
a field device configured to be installed in a plant and perform at least one of a measurement and a control which are necessary for controlling the plant;
a controller, according to claim 1, configured to control the plant by transmitting the process data to the field device and receiving the process data from the field device; and
a manager configured to manage a state of the plant by collecting the field data from the field device, said manager comprising:
a calculator configured to receive field data indicating a state of a field device installed in a plant and vital data indicating biological information of a plant worker, the field data being received from the field device, the vital data being received from the plant worker, the calculator calculating first index data and second index data, the first index data indicating a gap between a current one of the field data and a previous one of the field data which is received when the plant is in a normal state, the second index data indicating a gap between a current one of the vital data and a previous one of the vital data which is received when the plant is in the normal state; and
a determiner configured to determine health of the plant by using the first index data and the second index data which are calculated by the calculator, the health of the plant including an abnormal state, an unstable state, and a normal state,
wherein the determiner is configured to determine the health of the plant based on a magnitude relation between the first index data and a first threshold value set to the first index data and a magnitude relation between the second index data and a second threshold value set to the second index data,
wherein the determiner determines that the plant is in the abnormal state in a case where the first index data exceeds a first threshold value,
wherein the determiner determines that the plant is in the unstable state in a case where the first index data does not exceed the first threshold value and the second index data exceeds a second threshold value, and
wherein the determiner determines that the plant is in the normal state in a case where the first index data does not exceed the first threshold value and the second index data does not exceed the second threshold value.

18. A data processing method comprising:
receiving process data which is necessary for controlling a plant from a field device installed in the plant;
receiving vital data which is biological information of a plant worker from the plant worker;
calculating first index data and second index data, the first index data indicating a gap between a current one of the process data and a previous one of the process data which is received when the plant is in a normal state, the second index data indicating a gap between a current one of the vital data and a previous one of the vital data which is received when the plant is in a normal state;
determining health of the plant by using the first index data and the second index data, the health of the plant including an abnormal state, an unstable state, and a normal state;
determining the health of the plant based on a magnitude relation between the first index data and a first threshold value set to the first index data and a magnitude relation between the second index data and a second threshold value set to the second index data;
determining that the plant is in the abnormal state in a case where the first index data exceeds a first threshold value;
determining that the plant is in the unstable state in a case where the first index data does not exceed the first threshold value and the second index data exceeds a second threshold value; and
determining that the plant is in the normal state in a case where the first index data does not exceed the first threshold value and the second index data does not exceed the second threshold value.

* * * * *